US009334571B2

(12) United States Patent
Oh et al.

(10) Patent No.: US 9,334,571 B2
(45) Date of Patent: May 10, 2016

(54) METHOD OF FORMING INDIVIDUAL METALLIC MICROSTRUCTURES

(71) Applicant: Regents of the University of Minnesota, Minneapolis, MN (US)

(72) Inventors: Sang-hyun Oh, Plymouth, MN (US); Timothy W. Johnson, Shoreview, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 14/410,893

(22) PCT Filed: Mar. 13, 2013

(86) PCT No.: PCT/US2013/030804
§ 371 (c)(1),
(2) Date: Dec. 23, 2014

(87) PCT Pub. No.: WO2014/003843
PCT Pub. Date: Jan. 3, 2014

(65) Prior Publication Data
US 2015/0203969 A1 Jul. 23, 2015

Related U.S. Application Data

(60) Provisional application No. 61/666,301, filed on Jun. 29, 2012.

(51) Int. Cl.
C03C 25/10 (2006.01)
C23F 1/04 (2006.01)
H01L 21/02 (2006.01)
B81C 1/00 (2006.01)
B82Y 20/00 (2011.01)
(Continued)

(52) U.S. Cl.
CPC ............ *C23F 1/04* (2013.01); *B32B 43/006* (2013.01); *B81C 1/00111* (2013.01); *B82Y 20/00* (2013.01); *B82Y 35/00* (2013.01); *G01Q 60/22* (2013.01); *H01L 21/0259* (2013.01); *H01L 21/02603* (2013.01); *B32B 2311/02* (2013.01); *G01N 21/01* (2013.01); *G01N 21/658* (2013.01); *Y10T 156/1168* (2015.01)

(58) Field of Classification Search
CPC .... H01R 24/00; H01R 43/00; H01L 31/0352; H01L 3/018
USPC .............................. 216/39, 67; 438/738, 751
See application file for complete search history.

(56) References Cited

U.S. PATENT DOCUMENTS 7,696,102 B2 * 4/2010 Zhang ........................... 438/738
8,551,866 B2 * 10/2013 Moslehi et al. ............... 438/478
(Continued)

FOREIGN PATENT DOCUMENTS

CN 101623535 A 1/2010

*Primary Examiner* — Duy Deo
*Assistant Examiner* — Maki Angadi
(74) *Attorney, Agent, or Firm* — Kagan Binder, PLLC

(57) ABSTRACT

Methods for the formation of individual, precisely shaped nano- or micro-scale metallic structures, particularly pyramids. With this technique, mass fabrication of high-quality, uniform, and ultra-sharp pyramids, cones and wedges is achieved. The high yield, reproducibility, durability and massively parallel fabrication methods of this disclosure provide structures suitable for reliable optical sensing and detection and for cementing near-field optical imaging and spectroscopy as a routine characterization.

19 Claims, 9 Drawing Sheets

(51) Int. Cl.
*B82Y 35/00* (2011.01)
*G01Q 60/22* (2010.01)
*B32B 43/00* (2006.01)
*G01N 21/01* (2006.01)
*G01N 21/65* (2006.01)

(56) References Cited

U.S. PATENT DOCUMENTS

2010/0178810 A2* 7/2010 Aarts et al. .................... 439/676
2011/0055987 A1 3/2011 Moldovan
2012/0042510 A1 2/2012 Fussinger

* cited by examiner

Fig. 3A
Fig. 3B
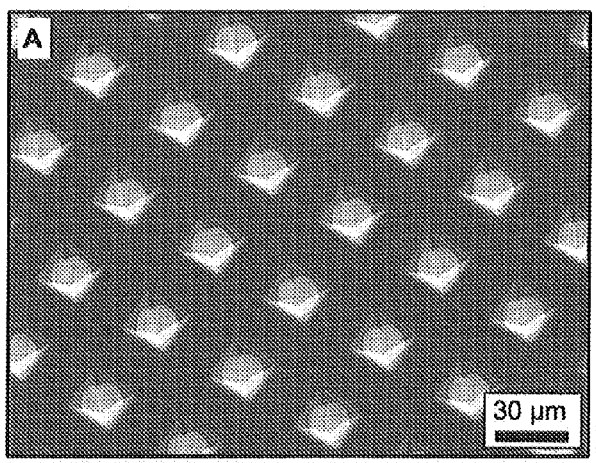
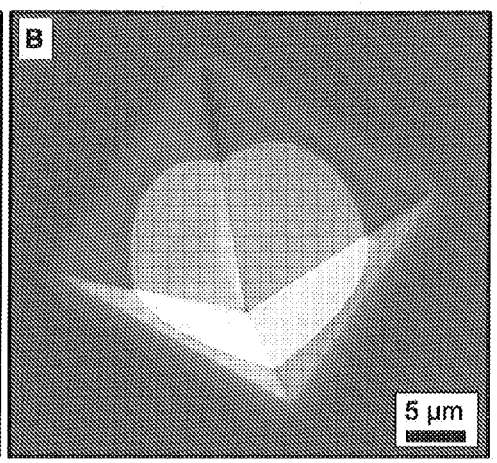
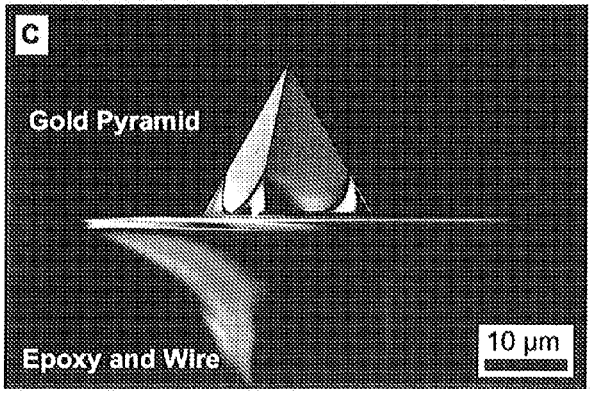
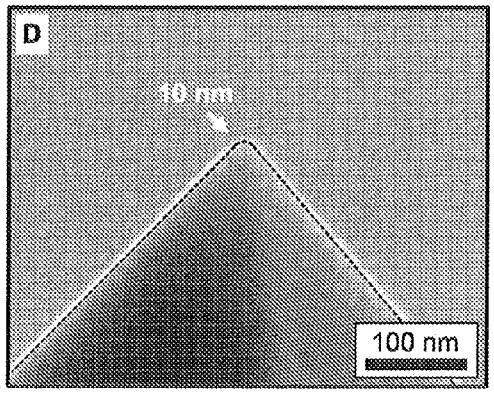
Fig. 4
Fig. 5

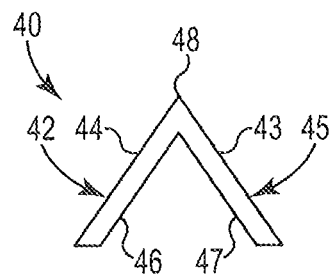
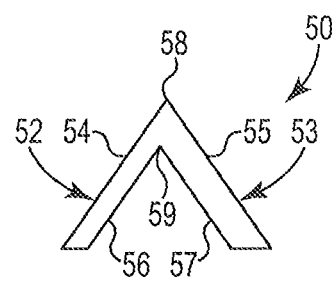
Fig. 6        Fig. 7
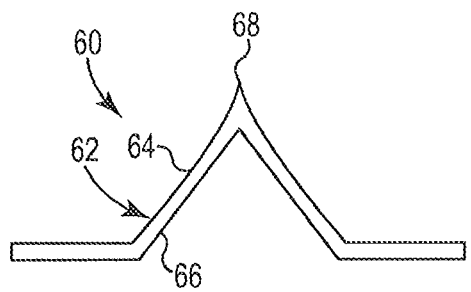
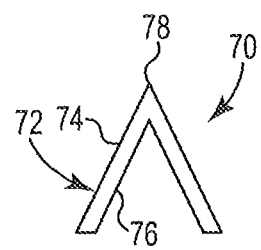
Fig. 8        Fig. 10
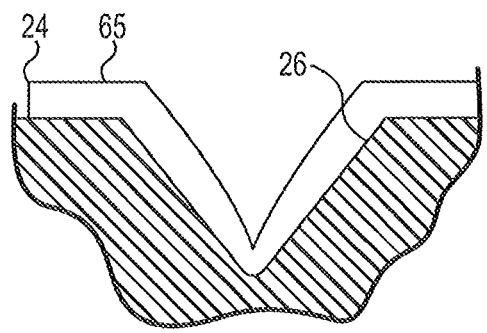
Fig. 9

METHOD OF FORMING INDIVIDUAL METALLIC MICROSTRUCTURES

CROSS REFERENCE TO RELATED APPLICATION

The present application claims priority to International Application No. PCT/US2013/030804, filed on Mar. 13, 2013, which in turn claims priority to U.S. Provisional Application No. 61/666,301, filed Jun. 29, 2012 entitled "Templated Mass Production of Ultra-Sharp Metallic Probes for Near-Field Optical Microscopy," the entire disclosures of which are incorporated herein by reference.

BACKGROUND OF THE INVENTION

The present invention relates generally to micro- and nano-scale patterned, metallic structures and methods of making such structures. More particularly, the present invention relates to metallic structures comprising precise, three-dimensional structures replicated from a patterned template substrate and methods of making such structures.

Several methods are known for fabricating patterned metal surfaces with features on a sub-micrometer or nanometer length scale. For example, in one method a metal film is deposited on a surface of a substrate such as by using thermal evaporation or sputtering. After depositions the metal film is patterned to have sub-wavelength scale features by conventional lithography steps such as by using photolithography or e-beam lithography. Alternatively, after deposition, focused ion beam (FIB) milling is used to pattern the metal film. Using either approach, sub-micrometer features can be formed in the metal film. These features, however, have several shortcomings. For example, one limitation is the surface roughness. Another limitation is the low throughput of lithography steps such as e-beam or FIB milling.

Additional known methods for fabricating patterned metal surfaces include nanoimprinting and nanomolding. Although nanoimprinting and nanomolding can pattern metals on the proper length scales, again, undesirable surface roughness is usually present in metal surfaces formed by nanoimprinting and nanomolding. In a typical proem, a patterned polymeric mold is filled with metal to form a replica. This produces undesirable surface roughness because metals do not easily wet the surfaces of the polymeric mold. Moreover, an additional shortcoming of nanoimprinting and nanomolding is that the polymeric mold needs to be etched away from the metal film to release the metal film. Accordingly, each mold can only be used once to produce a single metal film.

Another technique that can be used to fabricate smooth metal surfaces is generally referred to as template stripping. Template stripping utilizes the poor adhesion and good wettability of noble metals on solids such as mica, glass, and silicon. In a typical template stripping process, a freshly cleaved mica surface is coated with a film of gold. The exposed surface of the metal is then attached to another substrate with an epoxy adhesive. When the mica and substrate are separated the gold adheres to the substrate by the epoxy and is released by the mica surface. Such a method, however, is limited to use with generally flat surfaces and has not successfully been utilized with surfaces including three-dimensional features such as those typically found on patterned metal films. This is because the addition of three-dimensional features generally increases the area of mica in contact with gold. As this contact area increases it becomes more difficult to separate the gold film from the mica surface. Moreover, such three-dimensional features can interfere with separation of the gold from the three-dimensional surface features. Where a patterned metal having three-dimensional features is desired, the above nanoimprinting and nanomolding techniques are typically used wherein the mold is etched away from the metal film.

Yet another technique provides methods for replicating patterned metal films from a template substrate, the metal films being suitable for use in plasmonic devices and metamaterials. The template substrate is reusable and can provide plural copies of the structure of the template substrate. Moreover, because high-quality substrates that are inherently smooth and flat are available, patterned metal films can provide surfaces that replicate the surface characteristics of the template substrate both in the patterned regions and in the unpatterned regions. See, for example, PCT application WO 2010/065071 to the Regents of the University of Minnesota.

SUMMARY

The present disclosure provides advancements over conventional replicating and patterning techniques. This disclosure describes the formation of individual, precisely shaped nano- or micro-scale metallic structures. With this technique, mass fabrication of high-quality, uniform, and ultra-sharp pyramids, cones and wedges is achieved. The high yield, reproducibility, durability and massively parallel fabrication methods of this disclosure provide structures suitable for reliable optical sensing and detection and for cementing near-field optical imaging and spectroscopy as a routine characterization method.

Pyramidal, conical, and wedge structures formed in accordance with the present invention are smooth, highly reproducible, and comprise sharp tips with radii of curvature as small as 10 nm and even 5 nm, although smaller radii of curvature can be achieved.

The pyramids produced by the methods are suitable for single-molecule fluorescence imaging, tip-enhanced Raman spectroscopy (TERS), and other near-field or super-resolution imaging techniques. Single-molecule imaging with sub-20 nanometer spatial resolution and fluorescence enhancement factors of up to 200 can be achieved. Similar results can be obtained for TERS imaging of carbon nanotubes. Each pyramidal structure can be used on-demand, one at a time, and can be stored for extended periods of time without degradation.

A first particular embodiment of this disclosure is a method of making a plurality of three-dimensional, individual and unconnected metallic microstructures. The method includes masking a substrate (such as a silicon-based substrate or a semiconductor substrate) with a mask having a plurality of apertures therethrough, and etching the masked substrate to form a plurality of cavities in the substrate. The method further includes depositing a metallic layer over the mask and in the plurality of cavities in contact with the substrate, thus forming a metallic structure in each of the cavities. Subsequently, the method includes removing the metallic layer from over the mask, and removing the mask from the substrate to provide a plurality of individual metallic microstructures. A single step may used to remove the metallic layer from over the mask and the mask. Additionally or alternatively, the step of removing the metallic layer from over the mask may be done by physically stripping the metallic layer from the mask.

Another particular embodiment of this disclosure is a method of making a plurality of three-dimensional, individual and unconnected metallic microstructures. The method includes masking a substrate (such as a silicon-based substrate or a semiconductor substrate) with a mask having a plurality of apertures therethrough, and etching the masked substrate to form a plurality of cavities in the substrate. Subsequently, the method includes removing the mask from the substrate and applying a photoresist layer over the etched substrate, and then depositing a metallic layer over the photoresist and in the plurality of cavities in contact with the substrate, thus forming a metallic structure in each of the cavities. Rhe photoresist and the metallic layer are removed from the substrate to provide a plurality of individual metallic microstructures.

The metallic layer, and thus the resulting metallic microstructure, may comprise any of gold, silver, copper, tungsten, tantalum, molybdenum, titanium, nickel, cobalt, mixtures thereof and layers thereof. The silicon-based substrate may be a semiconductor material or a silicon wafer. In some embodiments, a non-silicon-based semiconductor substrate may be used. The individual metallic microstructures may be pyramids, cones, or wedges having a tip angle of 70.52 degrees, or, have a tip angle less than 70 degrees. The tip may have a radius of about 10 nm, or less than 10 nm, such as about 5 nm.

The microstructures, particularly those structures having an ultra-sharp tip, may have a protective coating such as aluminum oxide ($Al_2O_3$) applied on the metallic structure to inhibit molecular migration and tip dulling.

The microstructures may have graded, stepped or otherwise patterned sidewalls, formed by the cavity surface having the inverse topography on the sidewalls. The patterned sidewalls may be made, for example, by self-aligned stencil lithography.

The microstructures may include an aperture therethrough at the tip; such an aperture is particularly suited for embodiments when the microstructure is illuminated internally. The aperture may be a circular aperture, a slot, or a C-shaped aperture.

These and various other features and advantages will be apparent from a reading of the following detailed description.

BRIEF DESCRIPTION OF THE DRAWINGS

The invention may be more completely understood in consideration of the following detailed description of various embodiments of the invention in connection with the accompanying drawings, in which:

FIG. 3A is a scanning electron microscope (SEM) image of a plurality of high-quality, uniform, ultra-sharp, pyramidal metallic structures prior to being removed from the mold; FIG. 3B is an enlarged SEM image of a single pyramidal metallic structure prior to being removed from the mold.

FIG. 4 is an SEM image of a pyramidal metallic structure after being removed from the mold.

FIG. 5 is an SEM image of a side view of a pyramidal metallic structure.

FIG. 6 is a cross-sectional view of a metallic structure.

FIG. 7 is a cross-sectional view of another embodiment of a metallic structure.

FIG. 8 is a cross-sectional view of another embodiment of a metallic structure.

FIG. 9 schematically illustrates a step of a method for forming the metallic structure of FIG. 8.

FIG. 10 is a cross-sectional view of yet another embodiment of a pyramidal metallic structure.

DETAILED DESCRIPTION OF THE INVENTION

The present disclosure provides a method for mass fabrication of high-quality, uniform, ultra-sharp, metallic structures that have features and dimensions in the nano- and micro-scale. Briefly, the method includes masking a substrate (e.g., a monocrystalline substrate) with a mask that has at least one aperture, and etching the exposed substrate to create a cavity in the substrate. A metallic layer is deposited onto the mask and into the cavity in contact with the substrate. The mask, and the metallic layer present thereon, is stripped from the substrate, leaving the metallic layer and thus a three-dimensional structure in the cavity. A pyramidal metallic structure can be made from a symmetrical (e.g., circular) aperture in the mask, whereas an elongated metallic structure, such as a wedge, can be made from an elongated aperture in the mask. The resulting metallic structure is precise with smooth surfaces and sharp edges and corners. The precise shape of the resulting structure can be modified by the type of etching used, e.g., crystallographic etching, plasma etching, etc. and by modifying various steps. Additionally, the metallic structures can undergo various post-processing steps.

In the following description, reference is made to the accompanying drawings that form a part hereof and in which are shown by way of illustration several specific embodiments. The following description provides additional specific embodiments. It is to be understood that other embodiments are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples provided below.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Figure 1A:
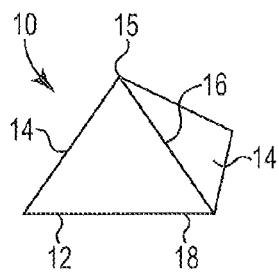
FIG. 1A is a schematic plan view of a pyramidal metallic structure.
Figure 1B:
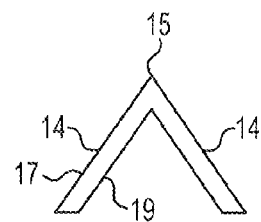
FIG. 1B is a cross-sectional view of the structure of FIG. 1A.

Referring to FIGS. 1A and 1B, a pyramidal metallic structure 10 is illustrated. Structure 10 has a base 12, sidewalls 14 that converge at tip 15, and wall edges 16 where adjacent sidewalls 14 intersection and base edges 18 wherein sidewalls 14 intersect with base 12. The particular structure illustrated, pyramidal structure 10, is a four-sided pyramid, having four sidewalls 14 of equal dimension and a square base 12. A wedge (not illustrated) would have two parallel sidewalls having a length greater than the other two sidewalls; the two elongate sidewalls would converge at an elongate tip. Returning to FIGS. 1A and 1B, sidewalls 14 and edges 16 are straight, uncurved, and high quality. Tip 15 is sharp, having a curvature of radius of, for example, less than 10 nm. Structure 10 has dimensions (both base 12 and sidewall 14 dimensions) of less than 10 micrometers, although structures having dimensions large as 50 micrometers could readily be made. Similarly, structures 10 with dimensions as small as 1 micrometer could readily be made. Additional discussion regarding the dimensions of structure 10 is provided below.

Seen in FIG. 1B, sidewalls 14 of structure 10 have an outer surface 17 and an inner surface 19. As will be apparent from the discussion below, outer surface 17 is defined by the surface of the cavity in which structure 10 is made. Outer surfaces 17 of sidewalls 14 intersect to form tip 15 with angle α. Sidewalls 14 have a thickness, between outer surface 17 and inner surface 19, of between 30 and 250 nm, although sidewalls 14 could be thicker or thinner, depending on the method of making structure 10 and the intended use of structure 10.

Structure 10 is formed by a template technique that has been shown to produce a variety of metallic structures, including ultra-sharp tips, with ultra-smooth patterned metallic surfaces. The structure is of such high quality because of the high-quality silicon or silicon-based mold in which it is made. In some embodiments, sidewalls 14 have a roughness that approaches that of the silicon mold, as measured by atomic force microscopy. For example, sidewalls 14 have a root mean square (rms) roughness of less than 1 nm (e.g., less than 0.9 nm, or less than 0.75 nm, or leaven less than 0.5 nm). The smoothness of the metal microstructure is generally limited by the silicon substrate and the method used to pattern the silicon template.

As an example, for a silicon substrate with a root mean square (rms) roughness of 0.19 nm, a roughness 0.65 nm was measured for a silver structure formed in that substrate, the largest contribution to this value being the grain boundaries in the polycrystalline silver. Within a single grain, the rms roughness was 0.26 nm, much closer to that of the silicon. No techniques were used, such as ultra-flat wafers or high-temperature deposition, to decrease the roughness.

Figure 2A:
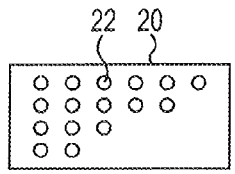
FIGS. 2A-2H schematically illustrate steps of a method for forming high-quality, uniform, ultra-sharp, metallic structures.
Figure 2B:
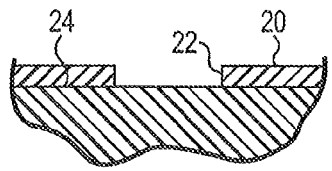

FIGS. 2A through 2H illustrate a method for making structure 10 in a silicon or silicon-based substrate. FIG. 2A shows a $Si_3Ni_4$ mask 20 (e.g., approximately 100 nm thick) with a plurality of apertures 22 therein. Apertures 22 are illustrated as circular, but may be any shape. Because the size of apertures 22 affects the size of the resulting structure 10, apertures 22 can be any size, although in most embodiments, apertures 22 are within the range of 1 to 50 micrometers. For a pyramidal structure, such as structure 10, apertures 22 have generally equal lateral and longitudinal dimensions; that is, apertures 22 generally symmetric in both direction; examples of such apertures 22 include circles and squares. For a wedge structure, the apertures are longer in one dimension that the other; examples of such apertures include rectangles. The distance between adjacent apertures 22 may be, for example, within the range of 25 to 100 micrometers, e.g., 50 micrometers. Apertures 22 can be formed by standard photolithography exposure, development, and etching, either prior to or after mask 20 is positioned on the silicon or silicon-based substrate (e.g., silicon wafer, glass, or Si substrate) which will eventually be the mold. In FIG. 2B, mask 20 with aperture 22 is positioned on a conventional silicon wafer 24.

Figure 2C:
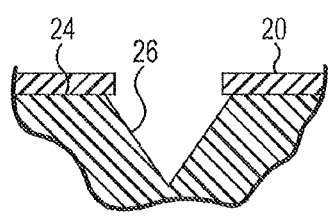

A subsequent crystallographic etch, such as with potassium hydroxide (KOH), creates inverted pyramidal cavities 26 in Si wafer 24 (FIG. 2C). This anisotropic etching process exposes the {111} crystal facets of the silicon, which join to form an open angle of 70.52 degrees. The etching process and recipe will affect the smoothness and sharpness of the sidewalls and edges. An example of a suitable process includes prolonged over-etching (1 hour or more) in a mixture of 30% KOH, 10% isopropyl alcohol (IPA) and water at 80° C.

Figure 2D:
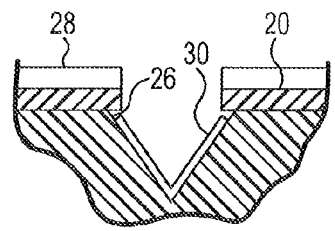

In FIG. 2D, a metal is deposited over mask 20 and into cavity 26, resulting in a metal layer 28 and metal structure 30. The metal can be any of the noble metals like silver, gold, copper, tungsten, tantalum, molybdenum, and titanium, as well as refractory metals, semiconductors, oxides, and magnetic materials, for example, and can be applied by, for example, evaporation or sputtering. In some embodiments, metal layer 28 and metal structure 30 may be formed of multiple layers and/or of multiple metals. As illustrated in FIG. 2D, metal structure 30 is not connected to metal layer 28, but is separate therefrom. This occurs when cavity 26 undercuts mask 20, resulting in a portion of cavity 26 positioned below and thus masked by mask 20.

Figure 2E:
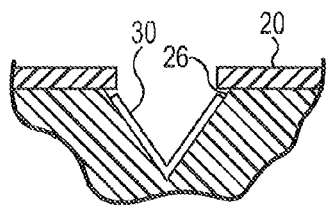
Figure 2F:
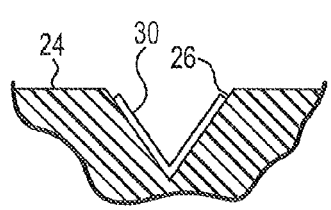

After the metal deposition (FIG. 2D), metal layer 28 is removed (e.g., stripped or physically lifted off), leaving mask 20 and metal structure 30 in cavity 26, as seen in FIG. 2E. Metal layer 28 may be removed by chemical methods, or may simply be removed by physically stripping or peeling layer 28 off. For example, an adhesive and its carrier may be applied to layer 28 and then pulled off after sufficiently adhered to layer 28, resulting in layer 28 being removed with the adhesive and its carrier. Cellophane tape and Scotch® tape are examples of suitable pressure-sensitive adhesive products that can be used to remove metal layer 28. After removal of metal layer 28, mask 20 is removed from wafer 24, for example, by a hydrofluoric acid lift-off bath, leaving metal structure 30 in cavity 26, as seen in FIG. 2F.

After removal of mask 20, remaining is Si wafer 24 with a metal structure 30 in each cavity 26. Multiple metal structures 30 may be removed at a time or metal structures 30 may be removed individually. To remove multiple structures 30, an adhesive material 32 (e.g., an epoxy) can be applied over Si wafer 24 and into cavities 26. Adhesive 32 has a higher bonding force with metal structure 30 than with wafer 24, thus allowing adhesive 32 to lift metal structure 30 out from cavity 26, as in FIG. 2H. Adhesive 32 can then be dissolved, releasing individual metal structures 30.

The above-outlined method is relative fast and cost efficient, as it does not require the use of slow and expensive nanofabrication tools such as FIB milling or electron-beam lithography. The use of standard photolithography allows parallel fabrication of thousands, hundreds of thousands, and even millions of metallic structures on a single 4 inch wafer, each with uniform properties. The thousands or millions of metallic structures can be simultaneously made, but individually retained for later use. FIG. 3A is a scanning electron microscope (SEM) image of a portion of a Si wafer having multiple, individual and unconnected metallic structures positioned in cavities in the wafer mold, and FIG. 3B shows a single structure in the mold.

FIG. 4 is a scanning electron microscope (SEM) image of a single pyramidal metallic structure removed from the mold and mounted on a 15 micrometer diameter tungsten wire. The single structure was removed from the mold cavity by attaching the wire to the structure with epoxy adhesive and then lifting the structure out of the mold.

FIG. 5 illustrates a metallic structure formed by the process described above; particularly, FIG. 5 shows the ultrasharp, nano-scale tip of the structure. In the illustrated embodiment, the tip has an angle of 70.52 degrees (due to the crystal facets of the silicon) with a radius of curvature of about 10 nanometers or less. It is noted that the large apex angle (i.e., 70.52 degrees) is particularly well suited for optical imaging applications, particularly to scatter near-field optical signals into far-field, as is discussed below. Additionally, the structures are particularly suited as probes for single-molecule fluorescence, single-molecule tip-enhanced Raman spectroscopy (TERS), and other techniques where the local field enhancement must be large and lateral imaging resolution must be high. It was found that over 95% of the metallic structure pyramids tested, made by the process described above, were useable for near-field imaging and provided similar resolution, both in fluorescence and Raman scattering. A method utilizing thermal oxidation of the silicon template, to adjust or tune the tip angle to an angle other than 70.52 degrees, if desired, is described below.

FIG. 6 schematically shows a cross-section of a pyramid structure made by the process described above; shown are two opposing sidewalls (e.g., sidewalls 14 of FIGS. 1A and 1B). Structure 40 has a first sidewall 42 having an outer surface 44 and an inner surface 46 that define a thickness there between. On the opposite side, structure 40 has a second sidewall 43 having an outer surface 45 and an inner surface 47 that define a thickness there between. The two sidewalls 42, 43 meet at tip 48. When crystallographic etching is used to form structure 40 in a Si wafer mold, tip 48 has an angle of 70.52 degrees. Structure 40 is symmetrical, and sidewalls 42, 43 have the same thickness.

An alternate embodiment is shown in FIG. 7, where a cross-section of an asymmetric pyramidal structure is shown. Structure 50 has a first sidewall 52 having an outer surface 54 and an inner surface 56 that define a thickness there between. On the opposite side, structure 50 has a second sidewall 53 having an outer surface 55 and an inner surface 57 that define a thickness there between. The two outer surfaces 54, 55 meet at tip 58 and the two inner surfaces 56, 57 meet at interior tip 59. When crystallographic etching is used to form structure 50 in a Si wafer mold, both tip 58 and interior tip 59 have an angle of 70.52 degrees. Although structure 50 is symmetrical on its exterior, sidewall 53 has a greater thickness than sidewall 52 and interior tip 59 is not aligned with tip 58. Structure 50 can be used for, e.g., optical applications that desire non-even or non-symmetric illumination.

Structure 50 is formed by generally the same steps as outlined above in reference to FIGS. 2B through 2H, except that the metal deposition (FIG. 2D) is applied at an angle to wafer 24 and cavity 26, rather than directly straight on or orthogonal thereto.

Another embodiment is shown in FIG. 8, wherein a cross-section of a symmetrical, yet non-linear pyramidal structure having an ultra-sharp tip is shown. Structure 60 has a sidewall 62 having an outer surface 64 and an inner surface 66. Two opposite sidewalls 62 meet at tip 68, which has an angle less than 70.52 degrees. For example, tip 68 may have an angle between about 27 and 70 degrees. Exemplary structures include tips that have an angle of 54 degrees and a radius of curvature of 33 nanometers, an angle of 54 degrees and a radius of curvature of 26.8 nanometers, an angle of 44.4 degrees and a radius of curvature of 14.3 nanometers, and an angle of 27.5 degrees and a radius of curvature of 8.9 nanometers. Additionally, both outer surface 64 and inner surface 66 are non-linear, having an arcuate portion proximate tip 68.

Structure 60 can be formed by generally the same steps as outlined above in reference to FIGS. 2B through 2H, except that prior to the metal deposition, the mask is removed and the surface of cavity 26 is oxidized (e.g., via thermal oxidation), forming a layer of $SiO_2$ in the cavity.

Because of the constricted area at the tip of cavity 26, the growth of the $SiO_2$ is hindered, leaving a sharp well at the bottom of cavity 26, as illustrated in FIG. 9. FIG. 9 shows cavity 26 in Si wafer 24 having a $SiO_2$ layer 65 lining cavity 26. The thickness of $SiO_2$ layer 65 is generally constant except for near the tip of cavity 26, where $SiO_2$ layer 65 narrows in thickness. The angle of the resulting tip can be tuned by adjusting the thickness of the $SiO_2$. After $SiO_2$ layer 65 is present, the entire surface of $SiO_2$ layer 65 can be coated with a metal layer (e.g., Au, Ag). The metal in the cavities can then be masked with a photoresist to protect the structures from a subsequent etching step, which removes the metal connecting the structures. The remaining metal structure can be removed by filling the structure with adhesive (e.g., epoxy) and pulling the structure from the cavity.

Alternately, structure 60 can be formed by, after forming cavities 26, coating and then patterning photoresist on the Si wafer 24 so that only cavities 26 remain exposed. The surface of cavities 26 is oxidized (e.g., via thermal oxidation), forming a layer of $SiO_2$ in the cavity. After $SiO_2$ layer 65 is present in cavity 26, a metal layer (e.g., Au, Ag) can be applied, and then the photoresist is removed. Alternatively, other layers that do not adhere well to metal(s) can be deposited on the silicon to reshape the tips and edges of the pyramid.

Onto this structure, photoresist layer (e.g., photoresist layer 88 of FIG. 11E) is applied over wafer 84 and oxide layer 96, and then metal is deposited. The resulting metallic structure has non-linear side walls, such as structure 60 of FIG. 8.

The previous embodiments of the structures (e.g., structure 10 of FIGS. 1A and 1B, structure 40 of FIG. 6, structure 50 of FIG. 7, and structure 60 of FIG. 8) have all been four sided pyramids. FIG. 10 shows an embodiment of a cone, having a circular base. Similar to the pyramidal embodiments, conical structure 70 of FIG. 10 has a sidewall 72 having an outer surface 74 and an inner surface 76, both which are linear in this embodiment. Sidewall 72 forms a tip 78, which has an angle, for example, between about 27 and 70 degrees. Again similar to the pyramidal embodiments, structure 70 is formed by a technique that has been shown to produce a variety of metallic structures, including ultra-sharp tips, with ultra-smooth patterned metallic surfaces.

Conical structure 70 can be made by the following method. A cylindrical cavity is formed in a silicon-based substrate (e.g., Si wafer) using photolithography and plasma etching (similar to the process of FIGS. 2A through 2C). A conformal dielectric film (such as $SiO_2$ or $Al_2O_3$) is deposited on the exposed wafer surface. The sharp edges and walls of the cylinder will be covered with a coating of the film, forming a circular cross-sectional structure with non-linear or rounded walls, similar to that of FIG. 9. A metal layer is applied into the cavity (similar to the process of FIG. 2D), creating a sharp tip in the middle of the cavity. The dielectric film and metal are stripped (either sequentially, as per the process of FIGS. 2E and 2F, or in one step), resulting in a metallic, non-linear cone in the cavity. The radius of curvature of the tips of thus-formed metallic cones are as sharp as that of template-stripped pyramids (e.g., 5 nm, 10 nm).

Figure 11A:
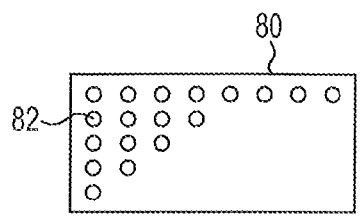
FIGS. 11A-11I schematically illustrate steps of a method for forming the metallic structure of FIG. 10.
Figure 11B:
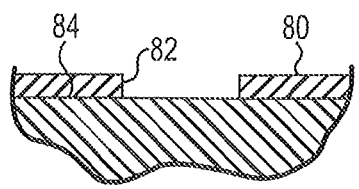
Figure 11C:
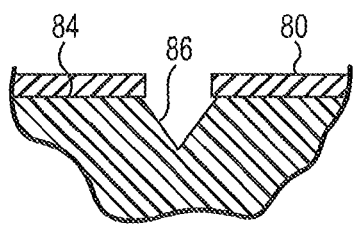
Figure 11D:
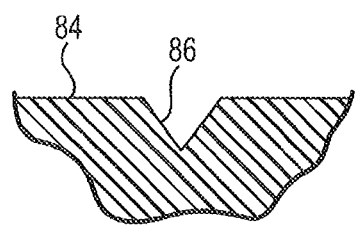
Figure 11E:
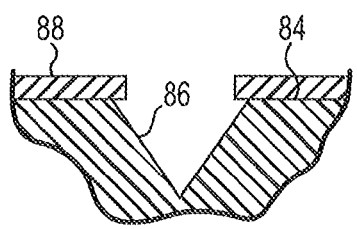

FIGS. 11A through 11I illustrate an alternate method for making pyramidal metallic structure 10. FIG. 11A shows a $Si_3Ni_4$ mask 80 (e.g., 100 DM thick) with a plurality of circular apertures 82 therein. Because the size of apertures 82 affects the size of the resulting structure 10, apertures 82 can be any size, although in most embodiments, apertures 82 are within the range of 10 to 50 micrometers. Apertures 82 can be formed by standard photolithography exposure, development, and etching, either prior to or after mask 80 is positioned on the wafer or other silicon-based substrate which will eventually be the mold. In FIG. 11B, mask 80 with aperture 82 is positioned on a conventional silicon wafer 84. A subsequent etch, such as a wet KOH etch, creates a pyramidal cavity 86 in Si wafer 84 (FIG. 11C).

In FIG. 11D, mask 80 has been removed from wafer 84 (e.g., via etching either hydrofluoric acid (HF) or phosphoric acid ($H_3PO_4$), or by physically stripping) leaving cavity 86. A photoresist layer 88 is applied over wafer 84 in FIG. 11E, leaving the area over cavity 86 open.

Figure 11F:
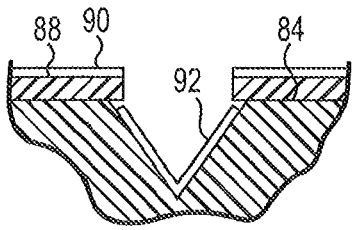
Figure 11G:
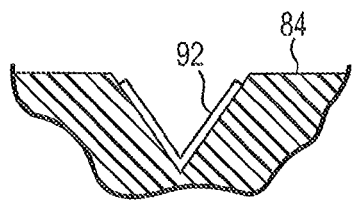
Figure 11H:
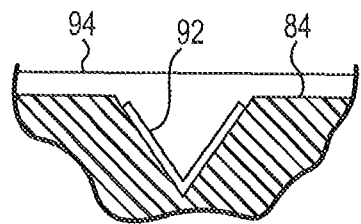
Figure 11I:
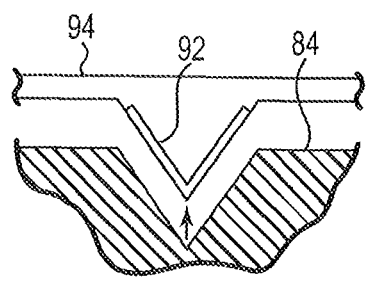

In FIG. 11F, a metal (e.g., silver, gold, copper, tungsten, tantalum, molybdenum, titanium, refractory metal, semiconductor, oxide, or magnetic material) is deposited (e.g., by evaporation or sputtering) over photoresist 88 and into cavity 86, resulting in a metal layer 90 on water 84 and metal structure 92 in cavity 86. After the metal deposition, metal layer 90 and photoresist 88 are removed, for example, by dissolving photoresist 88 in acetone or other suitable solvent, leaving wafer 84 with a metal structure 92 in each cavity 26.

Figure 2G:
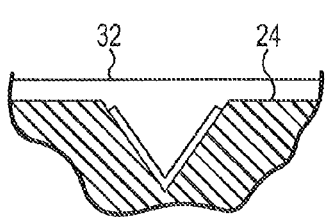
Figure 2H:
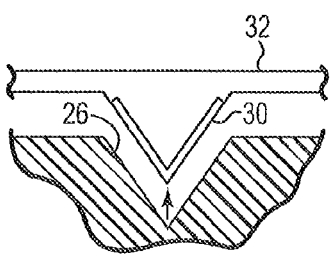

As described in above in respect to FIGS. 2G and 2H, multiple metal structures 92 may be removed at a time or metal structures 92 may be removed individually. To remove multiple structures 92, an adhesive material 94 (e.g., an epoxy) can be applied over wafer 84 and into the cavities and metal structure 92. Metal structure 92 can then be lifted out from cavity 86, as in FIG. 11I, after which adhesive 94 can be dissolved, releasing individual metal structures 92. The remaining wafer 84 with cavities 86 can be reused.

Various alternate and optional features may be incorporated in to or in with the structures described above and/or made by the described methods.

Figure 11J:
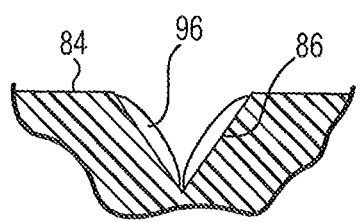
FIG. 11J is an alternate step of a method for forming an alternate metallic structure.

FIG. 11J illustrates a process where the surface of cavity 86 is oxidized (e.g., via thermal oxidation), forming a layer 96 of $SiO_2$ in cavity 86. Onto this structure, photoresist layer (e.g., photoresist layer 88 of FIG. 11E) is applied over wafer 84 and oxide layer 96, and then metal is deposited. The resulting metallic structure has non-linear side walls, such as structure 60 of FIG. 8. Additionally, the resulting metallic structure has a tip (e.g., tip 68 of FIG. 8) that is less than 70.52 degrees. For example, tip 68 may have an angle between about 27 and 70 degrees. Exemplary structures include tips that have an angle of 54 degrees and a radius of curvature of 33 nanometers, an angle of 54 degrees and a radius of curvature of 26.8 nanometers, an angle of 44.4 degrees and a radius of curvature of 14.3 nanometers, and an angle of 27.5 degrees and a radius of curvature of 8.9 nanometers.

Figure 11K:
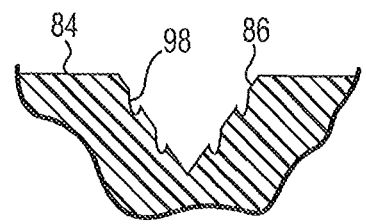
FIG. 11K is another alternate step of a method for forming another alternate metallic structure.

As another variation, the metallic structure may have graded, stepped or otherwise patterned sidewalls, formed by the cavity surface having the inverse topography on the sidewalls. The patterned sidewalls may be made, for example, by self-aligned stencil lithography. FIG. 11K illustrates a process where the surface of cavity 86 includes a plurality of topographical features 98. Onto this structure, photoresist layer (e.g., photoresist layer 88 of FIG. 11E) is applied over wafer 84 and cavity 86 with features 98, and then metal is deposited. The resulting metallic structure has sidewalls with the inverse pattern of features 98.

Figure 12:
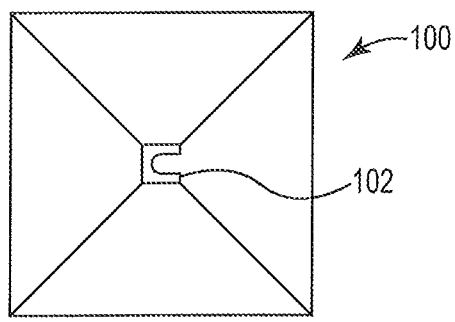
FIG. 12 is a top view of an embodiment of a pyramidal metallic structure configured for internal illumination.
Figure 13:
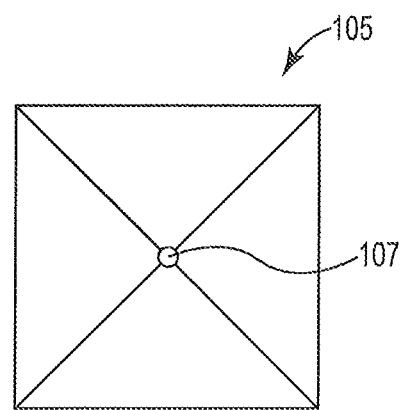
FIG. 13 is a top view of another embodiment of a pyramidal metallic structure configured for internal illumination.

As indicated briefly above, the ultra-sharp and ultra-smooth metallic structures are particularly suited for optical sensing and detection and in near-field optical imaging and spectroscopy. In some of these applications, the structures, particularly their tips, are illuminated externally. In other applications, the structures can be illuminated internally; in the embodiments where the structures are illuminated internally, the structure is preferably filled with an optically transparent material, such as transparent epoxy. In FIGS. 12 and 13, two embodiments of pyramidal structures adapted for internal illumination are illustrated. In FIG. 12, structure 100 has a C-shaped aperture 102 located at the tip or apex of structure 100, and in FIG. 13, structure 105 has a circular aperture 107 located at the tip or apex of structure 105. Such apertures 102, 107 can be formed via focused ion beam (FIB) milling of the metal layer while still in the cavity (see, for example, FIG. 2F, which illustrates metal structure 30 in cavity 26). See, for example, "Ultrahigh light transmission through a C-shaped nanoaperture" by Xiaolei Shi, Lambertus Hesselink and Robert Thornton (Optics Letters, Vol. 28, No. 15, pp 1320-1322, Aug. 1, 2003).

As yet another option, particularly for those structures having an ultra-sharp tip (e.g., tip angles of about 45 degrees or less, or, a tip with a radius of 5 nm or less), a protective coating can be applied on the metallic structure to inhibit molecular migration and tip dulling. For example, a sharp gold tip will dull over time due to the atomic migration of the Au molecules. A suitable protective coating is an ultra-thin (i.e., less than 5 nm thick, in some embodiments about 2 nm thick) coating of aluminum oxide ($Al_2O_3$). A 2 nm thick $Al_2O_3$ coating on Au can maintain a 2 nm radius on the tip.

As indicated briefly above, the metallic structures are particularly suited for optical sensing and detection and in near-field optical imaging and spectroscopy. The following discussion provides details of near-field and Raman imaging experiments.

Figure 14:
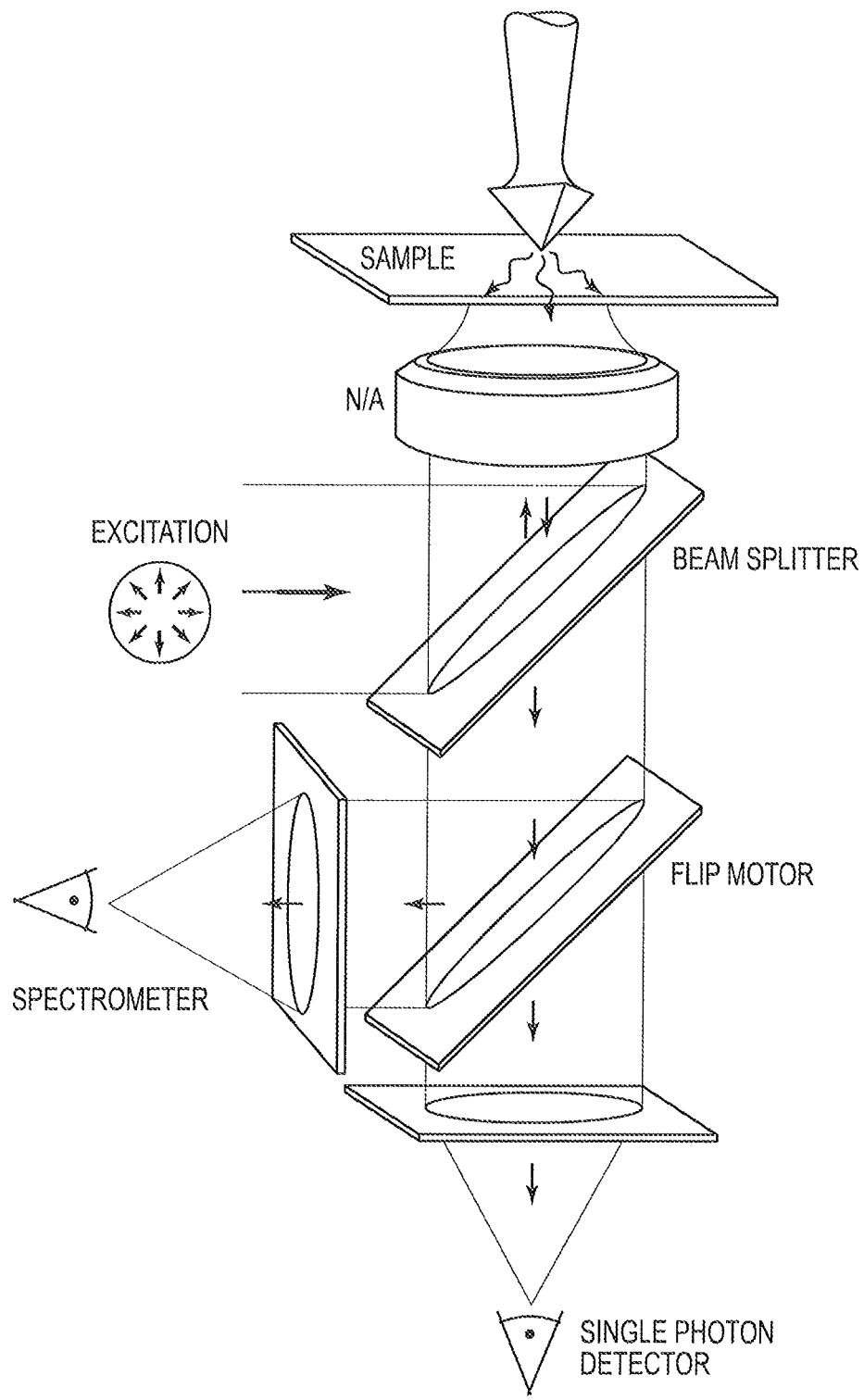
FIG. 14 is a schematic side view of a set-up used for near-field imaging.

FIG. 14 illustrates an experimental set-up used for near-field imaging using a pyramidal structure. The sample to be viewed is placed onto an x-y piezo scan-stage on top of an inverted confocal optical microscope. An atomic force microscope scan head is placed on top of the microscope, allowing the pyramidal nanostructure tip to be positioned in the center of the optical focus. A tightly focused radially-polarized optical excitation (i.e., laser beam) is used, providing a strong longitudinal electric field at the optical focus and giving maximum electric field enhancement from the pyramidal tip. The sample is raster-scanned below the pyramidal tip, allowing for simultaneous topographical and optical images. The tip—sample separation (approx. 5 nm) is maintained by using either shear-force or dynamic normal mode feedback. Photons emitted from the sample are collected by the objective and sent to either an avalanche photodiode (MD) or a spectrometer and liquid nitrogen cooled charge coupled device (CCD).

Figures 15A, 15B, 15C:
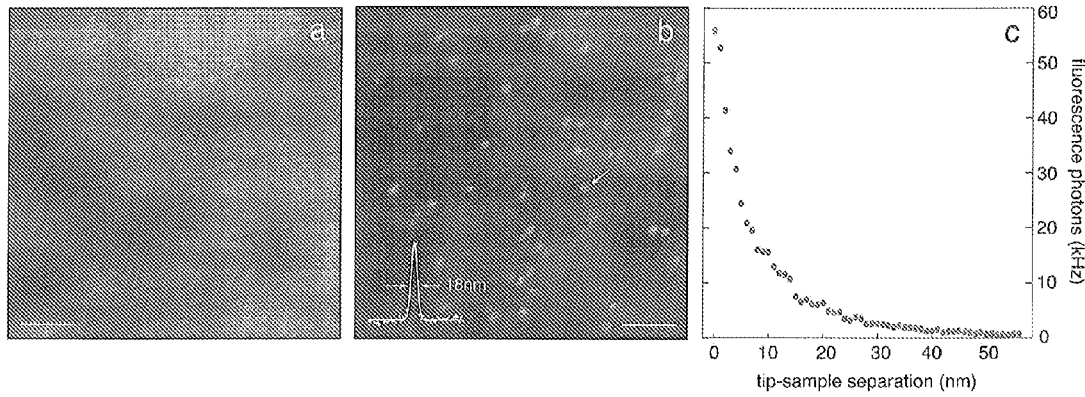
FIGS. 15A and 15B are images from near-field fluorescence imaging.
FIG. 15C is a graph showing the fluorescence rate as a function of tip-molecule separation.

FIGS. 15A and 15B show corresponding confocal and near-field fluorescence images of single dye molecules recorded with a pyramidal nanostructure tip. FIG. 15A is the confocal fluorescence image (contrast enhanced 5-fold), and FIG. 15B is the near-filed fluorescence image of the same sample area acquired with a pyramidal nanostructure tip. The full-width-half maximum (FWHM) of individual fluorescence spots is 18 nm. In both FIGS. 15A and 15B, the scale bar is 200 nm.

In these experiments, a He—Ne laser ($\lambda$=632.8 nm, P=21 nW) was used to match the absorption line of Atto 647N dye molecules. The large fluorescence enhancement due to the pyramidal tip allowed for a very low near-filed imaging excitation power of 21 nW, minimizing unwanted photobleaching of molecules within the confocal excitation volume. Single dye molecule samples were prepared by spin-casting a dilute dye solution onto coverglass coated with a thin (approx. 2 nm) layer of polymer (PMMA) to increase the photo-stability of the dye molecules. In the detection path, a 650 nm long-pass filter was placed in front of the APD to reject the laser excitation.

Although the resolution of confocal fluorescence imaging was too limited to identify individual molecules, near-field fluorescence imaging not only resolved individual molecules but also identified the orientation of the molecular transition dipole axis. Molecules oriented along the axis of the pyramidal structure (z-axis) revealed an optical enhancement of around 200-fold and an optical resolution of 18 nm, both due to the pyramidal tip. In-plane molecules exhibited a characteristic double-lobe pattern, FIG. 15C shows the fluorescence emission rate of a single z-oriented dye molecule as a function of the pyramid-sample distance. A maximum fluorescence rate enhancement of approximately 200-fold was observed. The resolution and enhancement far exceeded that of an 80 nm gold sphere that has been used in previous near-field fluorescence imaging.

Pyramidal structure probes with nanostructure tips were also tested for near-field Raman imaging. The pyramidal structures of this disclosure allowed for higher measurement reproducibility than tips produced by chemical etching, and for better quantitative models because of the well-defined probe geometry. To demonstrate the feasibility of using the pyramidal structures for TERS and near-field Raman imaging, a sample of carbon nanotubes (CNTs) produced by arc-discharge method were used, because the same tube bundle can be located and measured repeatedly.

Figures 16A, 16B, 16C:
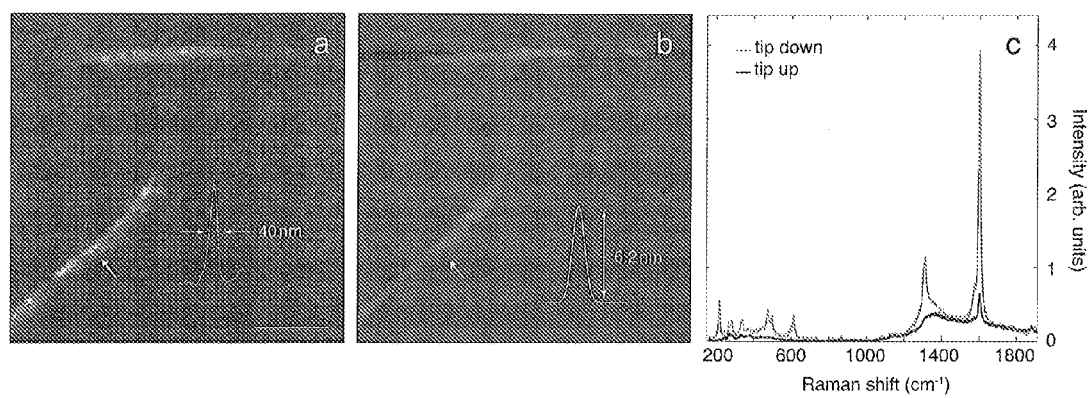
FIGS. 16A and 16B are images from near-field Raman imaging.
FIG. 16C is a graph shown the Raman scattering spectrum.

FIGS. 16A through 16C are directed to near-filed Ram scattering from single-wall carbon nanotube bundles grown by arc-discharge.

FIG. 16A shows a near-field image of the Raman G band (G-band intensity at $v=1600$ cm$^{-1}$) from the bundle, excited with a 785 nm laser, and the corresponding topographic image for an arc-discharge CNT bundle. The scale bar is 250 nm. The cross section of the near-field optical signal (arrow in FIG. 16A) yielded a width of 40 nm (see FIG. 16A inset). This 40 nm corresponds to the convolution of the optical field localization (the resolution) with the actual width of the nanotube bundle. The corresponding topographic image, FIG. 16B, shows a nanotube bundle width of 6.2 nm. The spectra of the CNT bundle with the tip close to the surface and retracted are shown in FIG. 16C. Taking the ratio of these two spectra for a Raman band, provides a measure of the enhancement factor, which in this case was approximately 10.

Finite-Difference Time-Domain (FDTD) calculations were performed for both pyramidal nanostructure tips and conical nanostructure tips of variable tip angle $\alpha$ and for different wavelengths $\lambda$. The calculations were used to determine the radiative properties of a quantum emitter placed in front of a tip. The tip was irradiated from the front by a focused higher-order laser beam. The same objective lens that was used for focusing was also used to collect photons due to the tip-sample interaction. Thus, it was evident that the signal-to-noise depends on the fraction of power that is radiated in the backwards direction, away from the tip and towards the objective lens. The fraction of power that was radiated in the forward direction coupled predominantly to surface plasmons propagating along the sides of the tip. The energy associated with these modes was ultimately dissipated to heat, although a structured tip shaft could be used to release some of this energy into the far-field.

To calculate the fraction of power radiated in a backwards direction, an electric dipole was placed at a distance of 3.75 nm in front of a gold nanostructure tip and used to evaluate the radiation patterns. The dipole orientation was parallel to the nanostructure tip axis. Perfectly matched layers were used at the boundaries to avoid spurious reflections and to evaluate the backwards radiation (BR) efficiency, defined as the power flux through the bottom half space (z<0) normalized with the corresponding power radiated by an isolated dipole in free space. Accordingly, the BR efficiency in absence of the tip was one. Calculations were performed for both pyramidal structures and conical structures with variable tip angles $\alpha$; the results were similar, and thus, only the data for pyramidal tips is shown in FIG. 16C. Note: a tip represents an infinitely extended structure and that terminating its length for computational reasons can generate severe artifacts. This is even the case if perfectly absorbing layers are used. It is thus necessary that the computational window is comparable to or larger than the surface plasmon propagation length. Because the latter increases with wavelength, memory and processing time constraints prevent accurate calculation of the BR efficiency at near-infrared wavelengths.

Figure 17A:
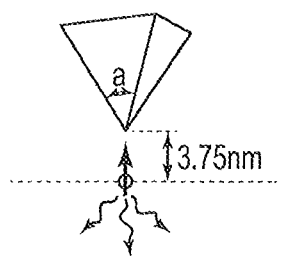
FIG. 17A is a schematic diagram illustrating a pyramidal nanostructure tip and a dipole.
Figure 17B:
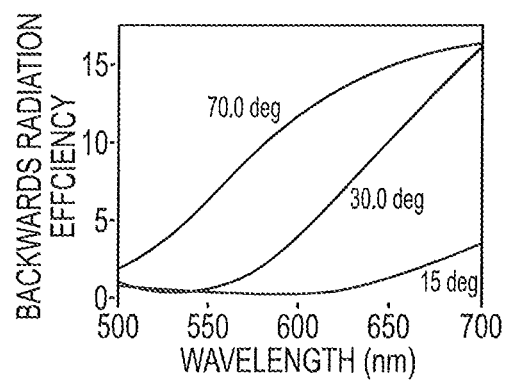
FIG. 17B is a graph showing the backwards radiation efficiency of the dipole as a function of wavelength.

Theoretical results, shown in FIGS. 17A and 17B, show that the BR efficiency increases as the wavelength $\lambda$ and the cone angle $\alpha$ is increased as expected, because plasmon propagation along the tip shaft becomes strongly mode-mismatched for large a. It was found that increasing the angle $\alpha$ from 10 to 70 degrees enhanced the backwards radiation by more than a factor of 10 at a wavelength of $\lambda=650$ nm. This enhancement was due not only to a redistribution of the radiation pattern but mostly to electromagnetic back-action, by which the tip enhances the dipole's ability to release energy. Thus, an enhanced BR efficiency corresponds to an increased radiative decay rate. This increased BR efficiency thus prevents a quantum emitter from complete quenching and allows high quality near-field fluorescence imaging on samples with single molecules.

Experimental Method

The following non-limiting procedure was used to form nanoscale pyramidal structures using template stripping techniques of the present disclosure.

First, 100 nm of low-stress nitride was grown on new Si wafers. A photoresist ("MEGAPOSIT SPR-955" photoresist, from Rohm and Haas) was spin-coated on the wafers and exposed with an i-line stepper (Canon 2500 i3) using a mask to produce 5, 10, 15, and 20 micrometer diameter holes. The photoresist was developed (using "MF CD 26" developer from Rohm and Haas) for 70 seconds using a spray developer ("CEE 200X from Brewer Science). Next, using the resist as an etch mask, the nitride was etched using a reactive ion etching system (model 320 from Surface Technology Systems) with CF$_4$. The resist was then removed with an oxygen plasma and the wafers were put in a bath of 30% KOH, 10% isopropyl alcohol, and water for 90 minutes at 80° C. for the anisotropic etching. After etching, the wafers were rinsed for 30 minutes and cleaned with a 1:1 solution of sulfuric acid and hydrogen peroxide, removing any excess KOH salt crystals, and dried. Next, 200 nm of Au was evaporated on the patterned wafers using an electron-beam evaporator (CHW, SEC600). Next, the wafers were soaked in 49% hydrofluoric acid for 20 min to remove the nitride mask, giving isolated Au pyramids.

Thus, embodiments of the METHOD OF FORMING INDIVIDUAL METALLIC MICROSTRUCTURES are disclosed. Presented is a highly reproducible and effective method for the fabrication of precise pyramidal nanostructures and assembly of high-quality near-field probes. The implementations described above and other implementations are within the scope of the following claims. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of making a plurality of three-dimensional metallic microstructures, the method comprising:
   masking a silicon-based substrate with a mask having a plurality of apertures therethrough;
   etching the masked substrate to form a plurality of shaped cavities within the substrate;
   depositing a metallic layer over the mask and into the plurality of shaped cavities in contact with the substrate, and thus forming a metallic structure within each of the cavities that is shaped by the shaped cavity;
   removing the metallic layer from over the mask;
   removing the mask from the substrate to provide a plurality of individual metallic microstructures.

2. The method of claim 1 wherein the step of etching the masked substrate comprises crystallographically etching the masked substrate to form a plurality of pyramidal cavities.

3. The method of claim 2 wherein the plurality of pyramidal cavities have a tip angle of 70.52 degrees.

4. The method of claim 1 wherein the step of removing the metallic layer from over the mask comprises physically stripping the metallic layer from the mask.

5. The method of claim 1 wherein the mask is a nitride mask and the step of removing the mask from the substrate comprises using an acidic bath.

6. The method of claim 1 wherein the metallic layer comprises gold, silver, copper, tungsten, tantalum, molybdenum, or titanium.

7. The method of claim 1 wherein the silicon-based substrate is a semiconductor material.

8. The method of claim 7 wherein the semiconductor material is a silicon wafer.

9. The method of claim 1, wherein the resulting plurality of individual metallic microstructures have a tip angle of 70.52 degrees.

10. The method of claim 1, further comprising, prior to depositing the metallic layer, oxidizing a surface of the cavity to provide a plurality of individual metallic microstructures having a tip angle of less than 70 degrees.

11. The method of claim 1, further comprising forming an aperture in the metallic layer in the cavity.

12. The method of claim 11 wherein forming the aperture in the metallic layer comprises focused ion beam (FIB) milling of the metallic layer.

13. The method of claim 1, further comprising a step of removing a plurality of the individual metallic microstructures from within the cavities of the substrate.

14. The method of claim 1, wherein the etching step includes undercutting the mask within the substrate, and the step of depositing a metallic layer includes forming the metallic structure as a separate element that is not connected to the metallic layer over the mask.

15. A method of making a plurality of three-dimensional metallic microstructures, the method comprising:
   masking a silicon-based substrate with a mask having a plurality of apertures therethrough;
   etching the masked substrate to form a plurality of shaped cavities within the substrate;
   removing the mask from the substrate and applying a photoresist layer over the etched substrate;
   depositing a metallic layer over the photoresist and into the plurality of shaped cavities in contact with the substrate, and thus forming a metallic structure within each of the cavities that is shaped by the shaped cavity;
   removing the photoresist and the metallic layer from the substrate to provide a plurality of individual metallic microstructures.

16. The method of claim 15 wherein the step of etching the masked substrate comprises crystallographically etching the masked substrate to form a plurality of pyramidal cavities.

17. The method of claim 16 wherein the plurality of pyramidal cavities have a tip angle of 70.52 degrees.

18. The method of claim 15, further comprising a step of removing a plurality of the individual metallic microstructures from within the cavities of the substrate.

19. The method of claim 15, wherein the etching step includes undercutting the mask within the substrate, and the step of depositing a metallic layer includes forming the metallic structure as a separate element that is not connected to the metallic layer over the mask.

* * * * *